United States Patent [19]

Mattingly

[11] Patent Number: 4,807,605
[45] Date of Patent: Feb. 28, 1989

[54] HALO TRACTION BRACE

[76] Inventor: Leslie G. Mattingly, 10761 E. Laurel Ln., Scottsdale, Ariz. 85259

[21] Appl. No.: 942,367

[22] Filed: Dec. 16, 1986

[51] Int. Cl.$^4$ .......................... A61F 5/04; A61F 5/02
[52] U.S. Cl. ...................................... 128/75; 128/927; 128/78
[58] Field of Search .................... 128/75, 84 R, 84 C, 128/87 B, 78, 69, 927, 92 VS, 924, 92 Z

[56] References Cited

U.S. PATENT DOCUMENTS

| | | | |
|---|---|---|---|
| 2,166,229 | 7/1939 | Anderson | 128/84 R |
| 3,336,922 | 8/1967 | Taylor | 128/75 |
| 3,669,102 | 6/1972 | Harris | 128/84 R |
| 3,724,452 | 4/1973 | Nitschke | 128/75 |
| 3,795,243 | 3/1974 | Miller | 128/75 |
| 3,957,040 | 5/1976 | Calabrese | 128/75 |
| 4,245,627 | 1/1981 | Mignard | 128/75 |
| 4,285,336 | 8/1981 | Oebser et al. | 128/75 |
| 4,383,523 | 5/1983 | Schurman | 128/75 |
| 4,444,179 | 4/1984 | Trippi | 128/75 |
| 4,541,421 | 9/1985 | Iversen et al. | 128/87 B |
| 4,620,530 | 4/1986 | Lanier et al. | 128/75 |
| 4,628,913 | 12/1986 | Lerman | 128/78 |

FOREIGN PATENT DOCUMENTS

| | | | |
|---|---|---|---|
| 227677 | 6/1959 | Australia | 128/75 |
| 3302078 | 7/1984 | Fed. Rep. of Germany | 128/75 |

Primary Examiner—David A. Wiecking
Assistant Examiner—Tonya Lamb
Attorney, Agent, or Firm—Gregory J. Nelson

[57] ABSTRACT

An orthopedic vest having a posterior and anterior portion fastenable at opposite sides of the user and which when fastened applies an inward force toward the sagittal plane of the body of the user. The vest adjustably supports front and rear yokes each having shoulder harness portions which are attachable over the shoulder of the user. Front and rear support rods are also secured to the anterior and posterior vest portion for adjustably securing a halo about the head of the user. Preferably the rods, halo and associated brackets are of a non-ferrous material for compatibility with CT, NMR and X-ray procedures. The halo consists of a ring having opposite temporal sections, a frontal section and a posterior section. The posterior section or loop is preferably elevated for access to the skull portion of the user. The halo receives skull pins at spaced-apart peripheral locations with the skull pins disposed at an angle with respect to the halo so as to be generally normal with the immediately associated skull portion against which the pin impinges.

15 Claims, 10 Drawing Sheets

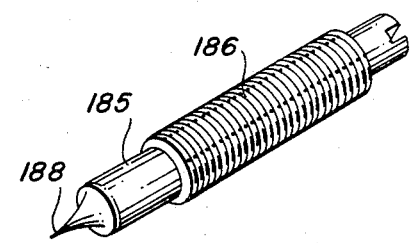
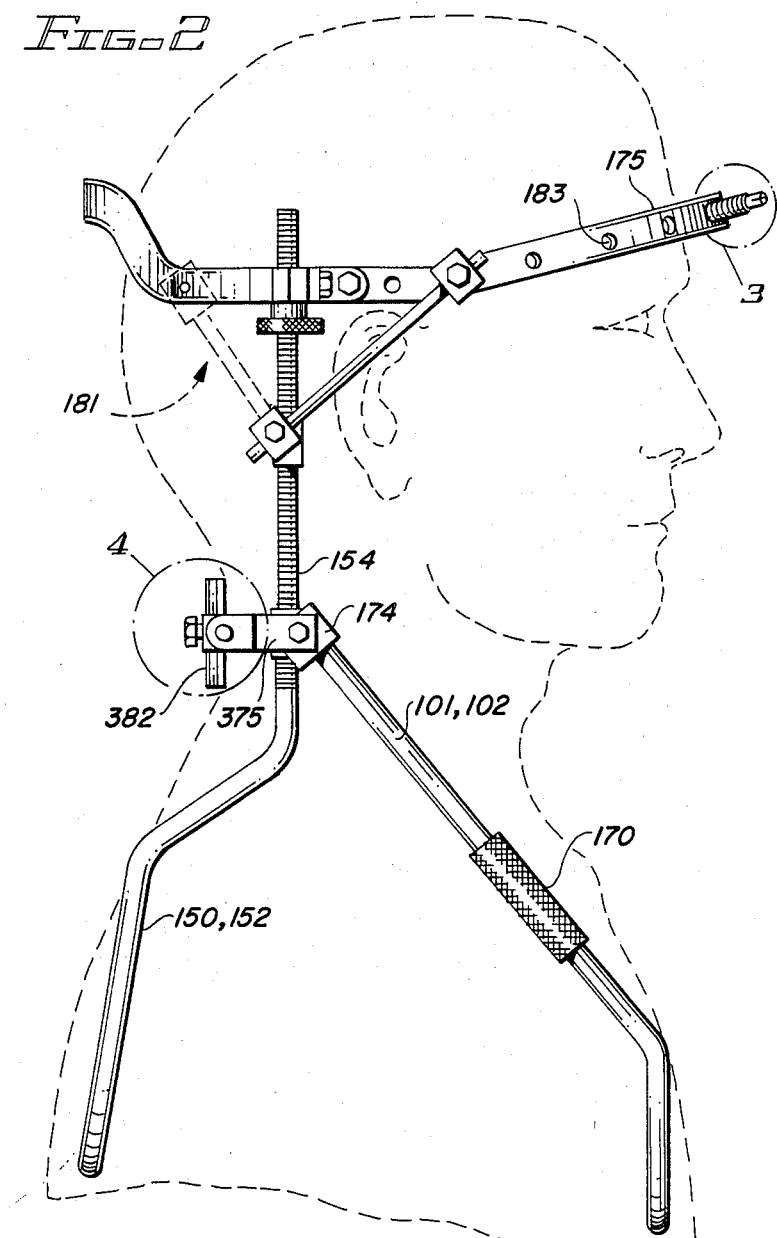
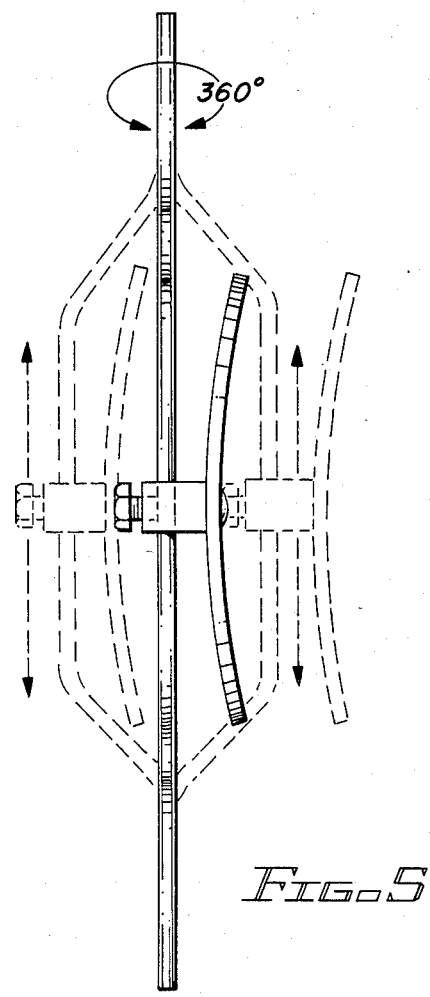
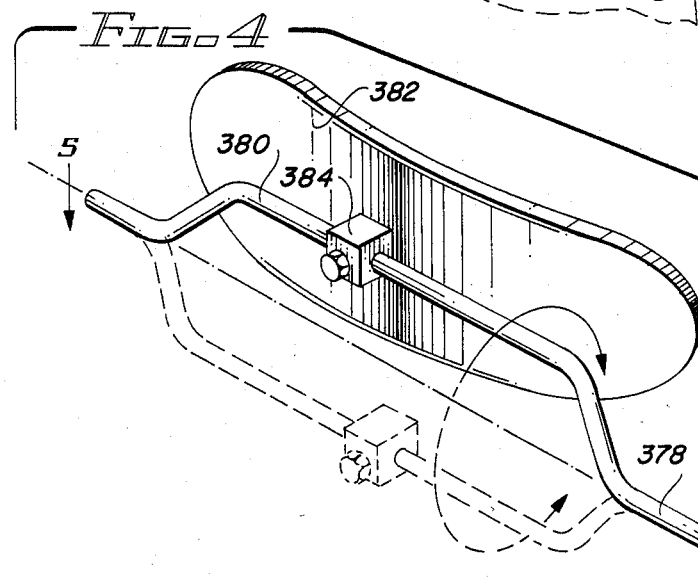

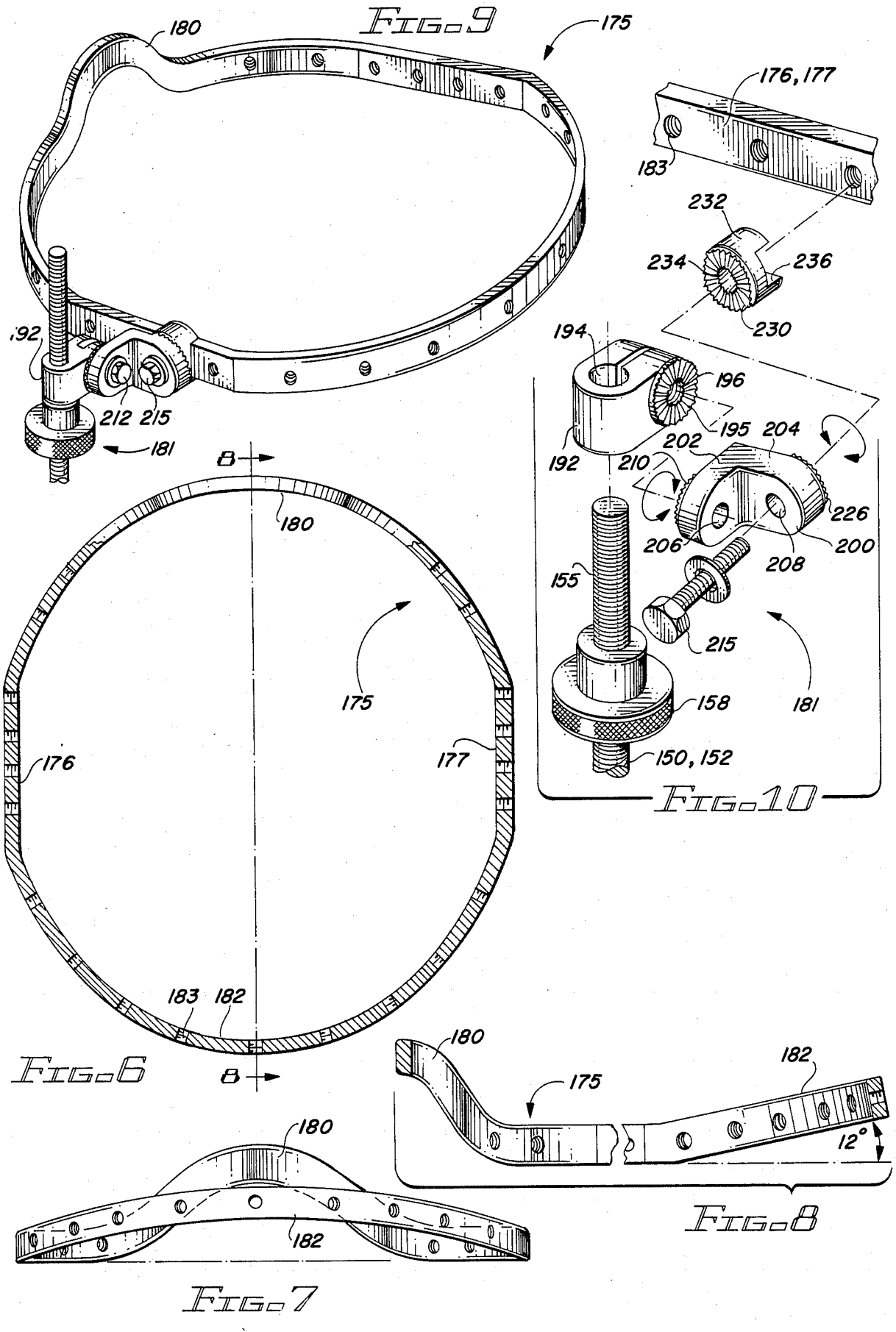

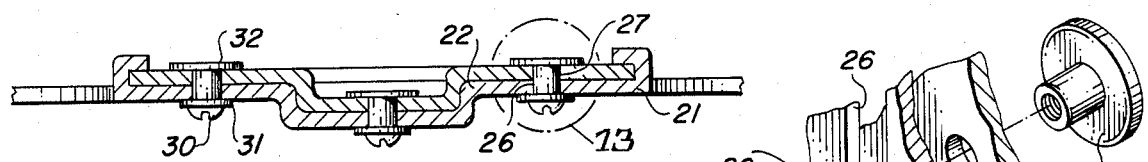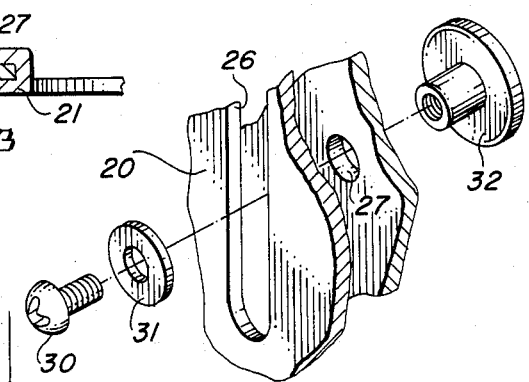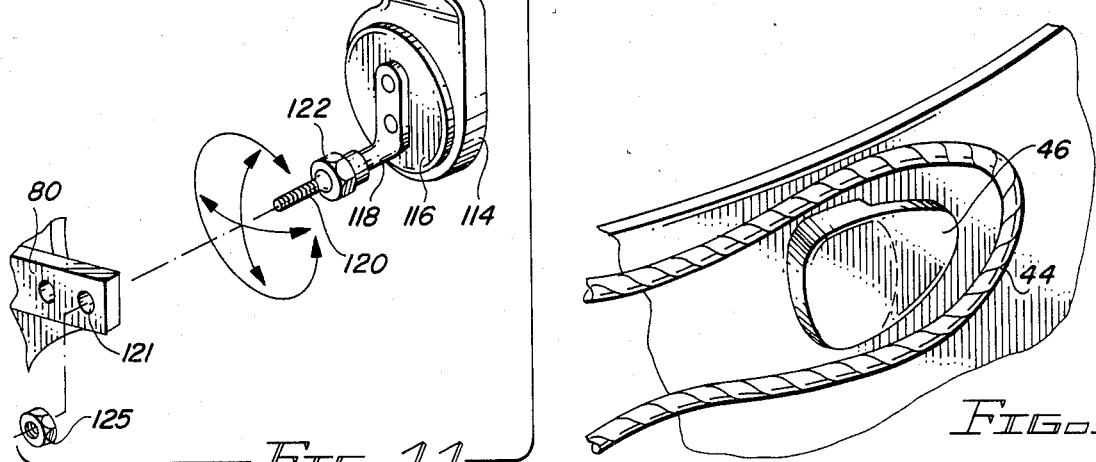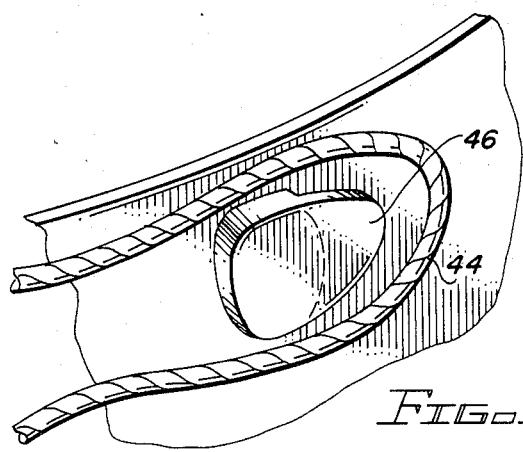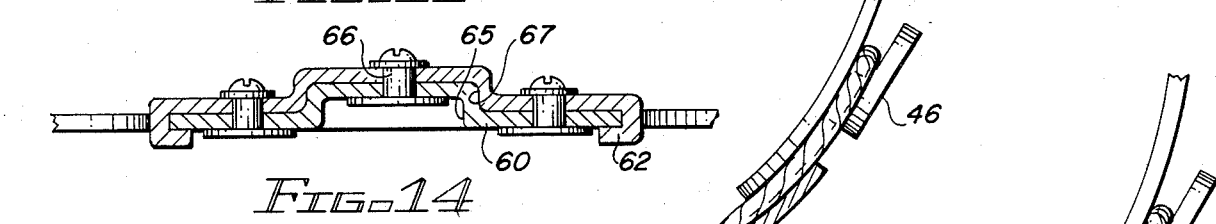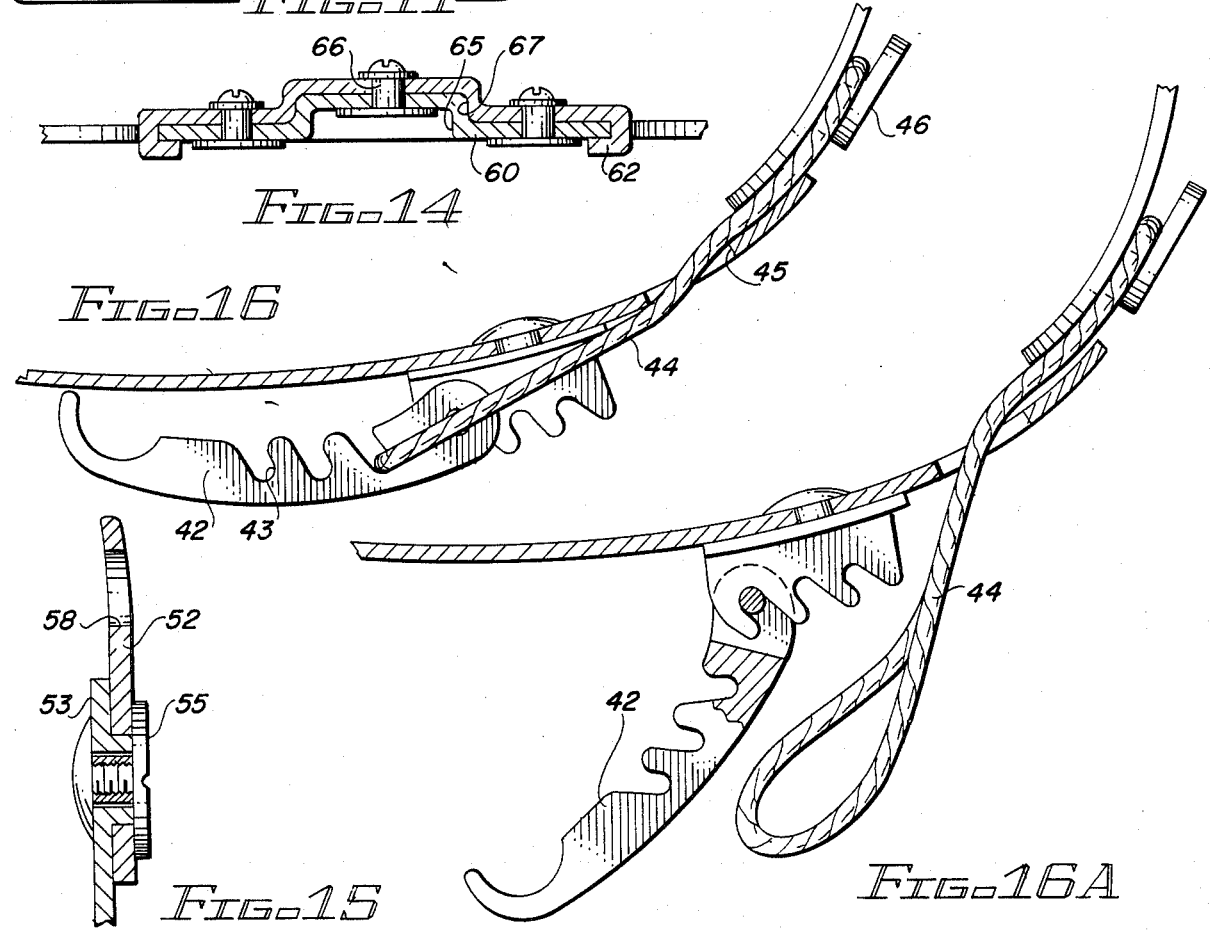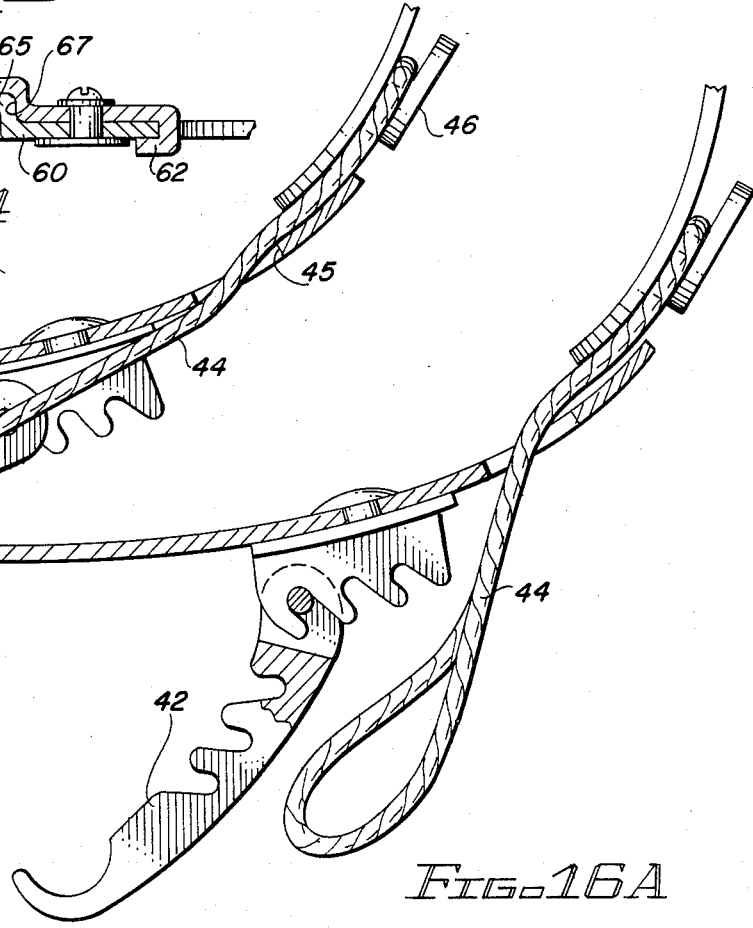

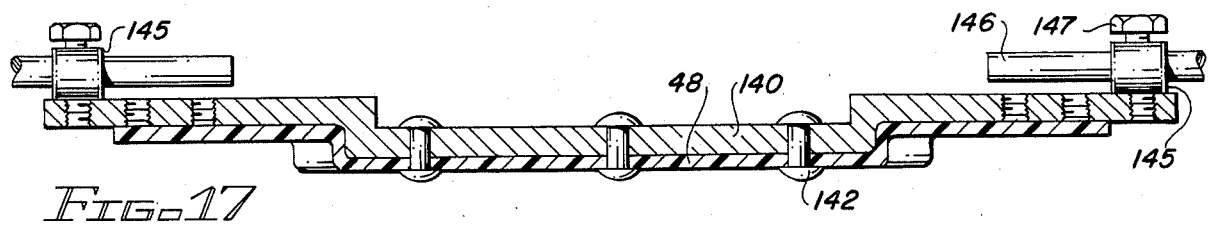
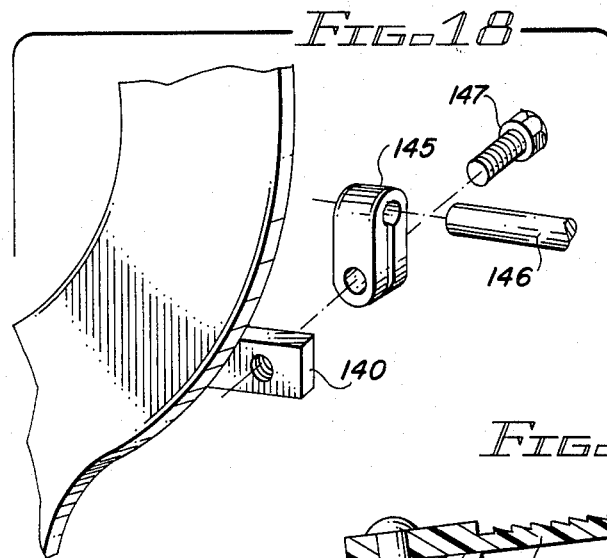

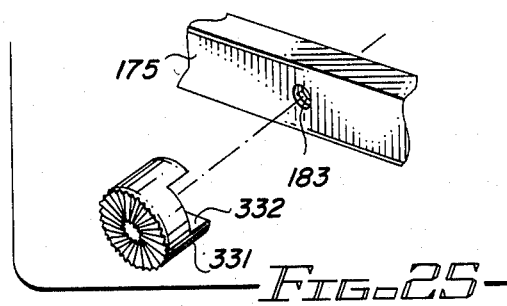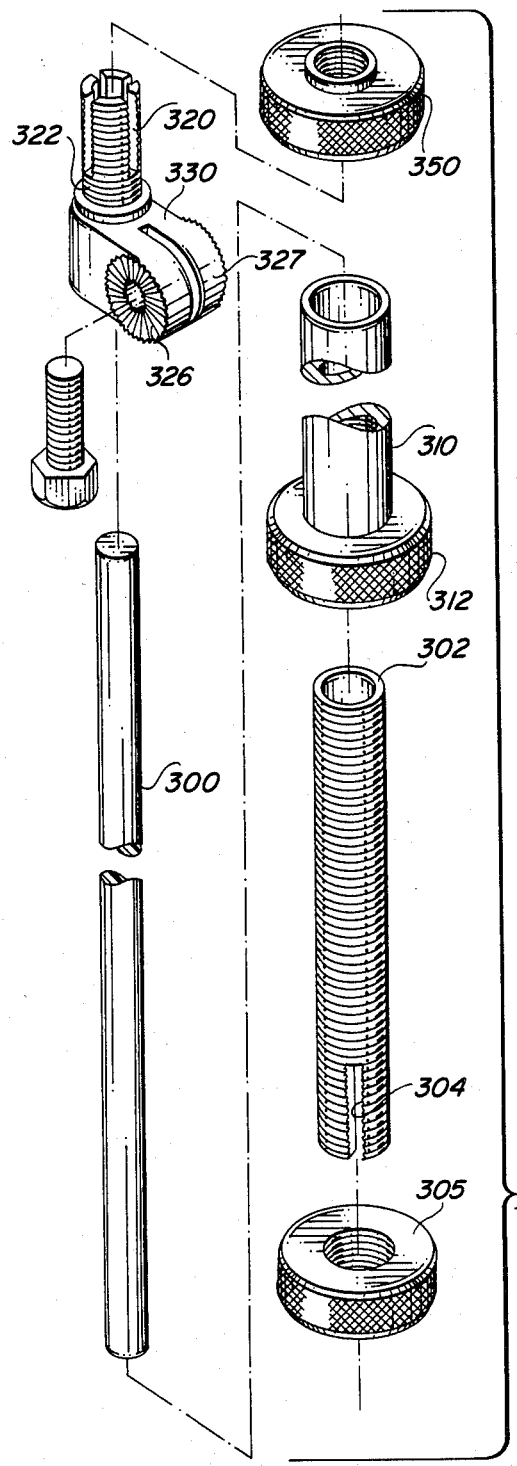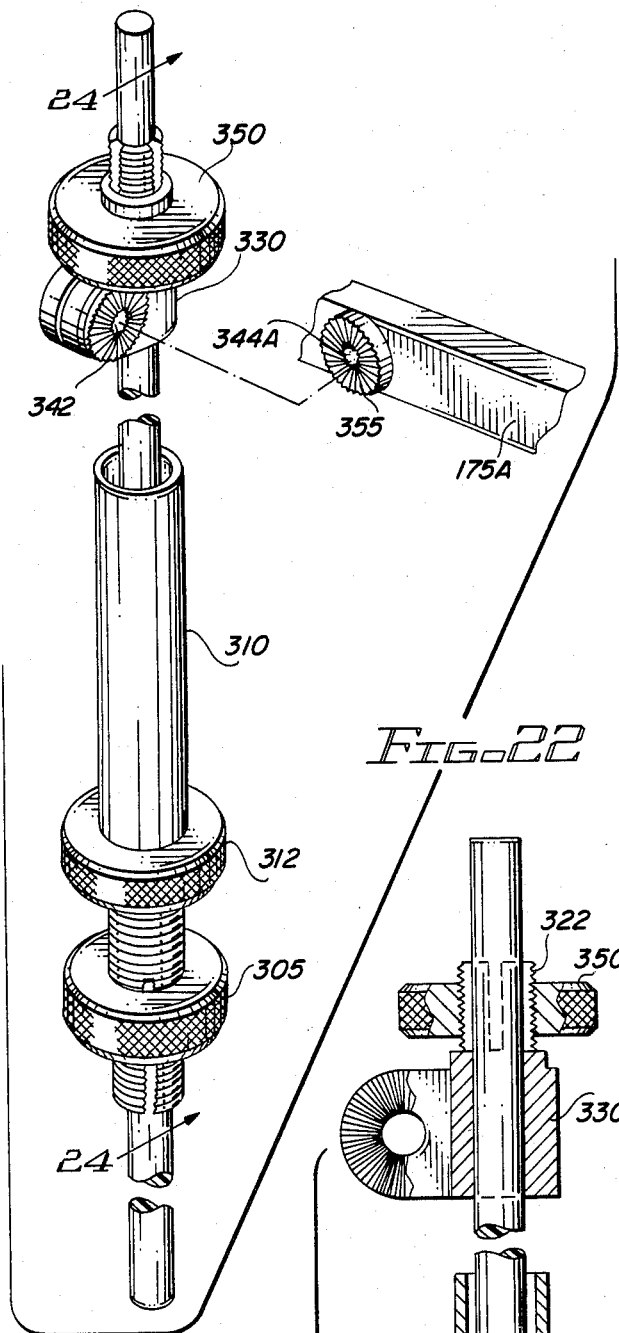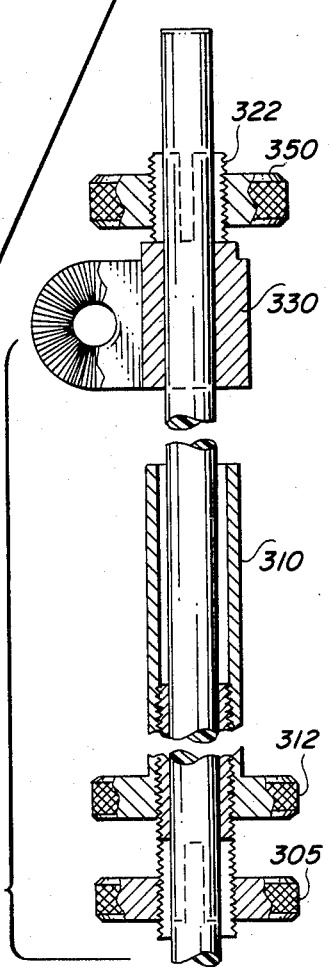

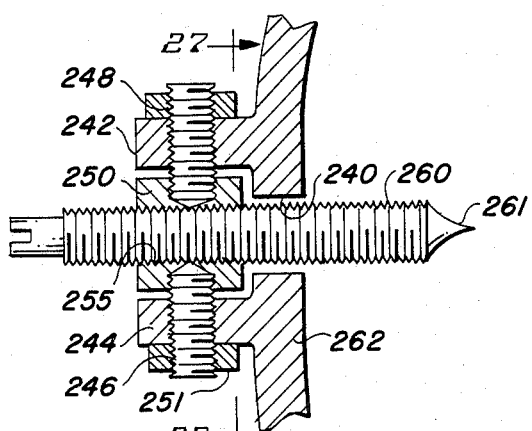
FIG.-26A
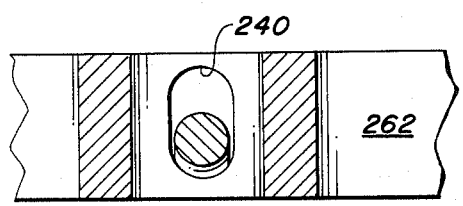
FIG.-27
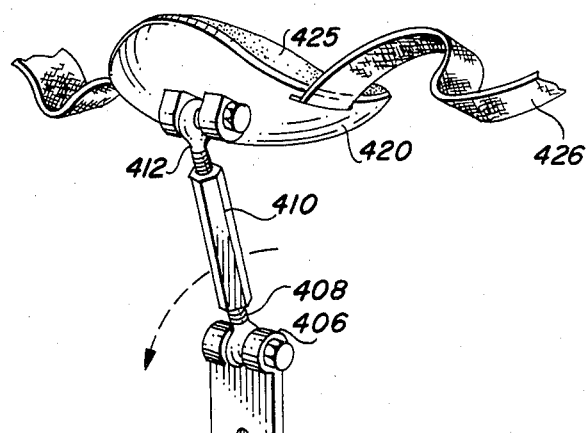
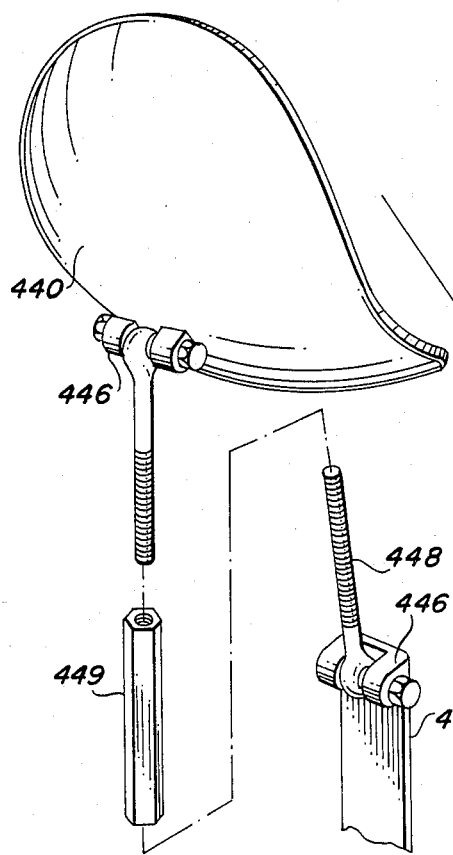
FIG.-28
FIG.-29

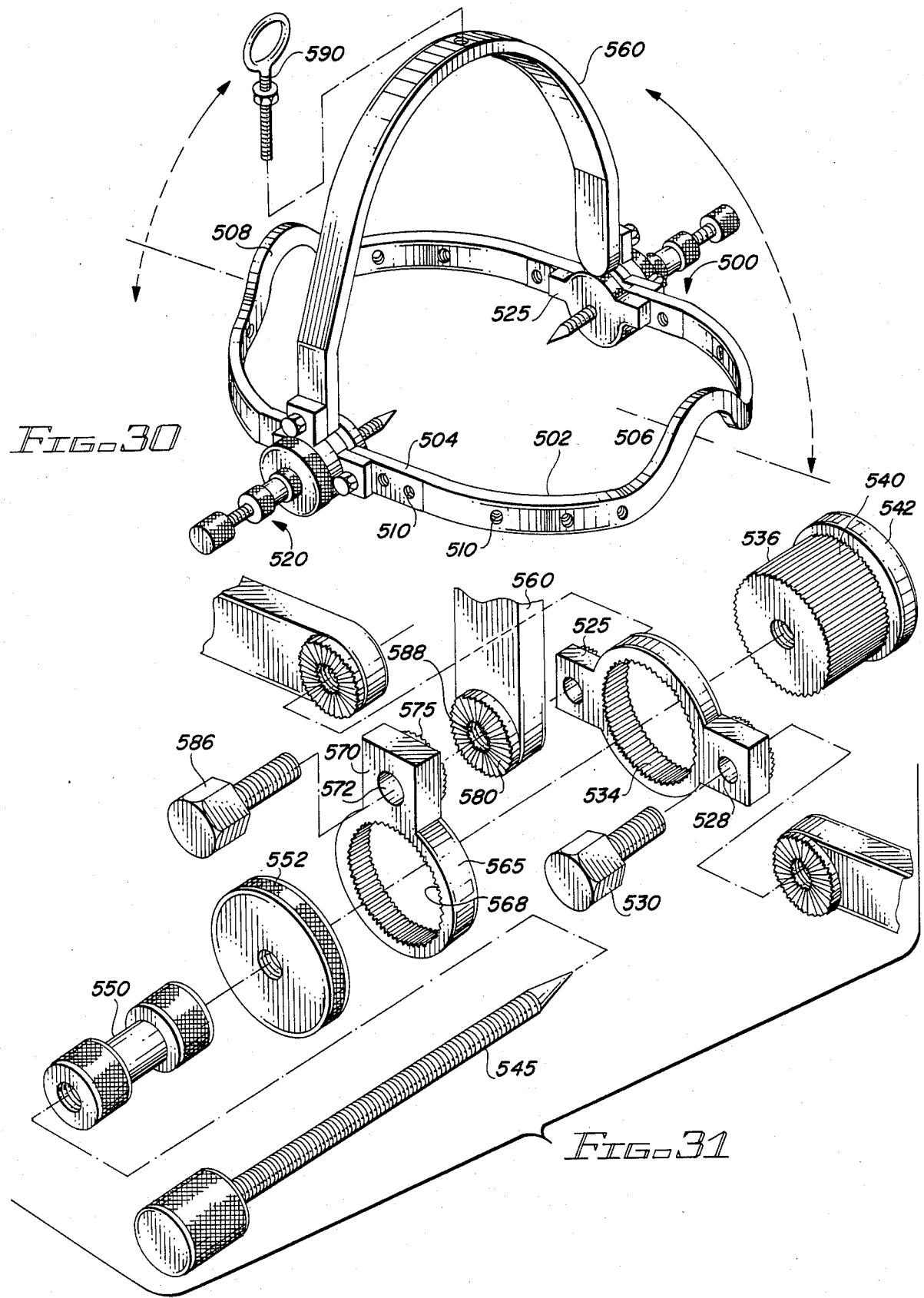

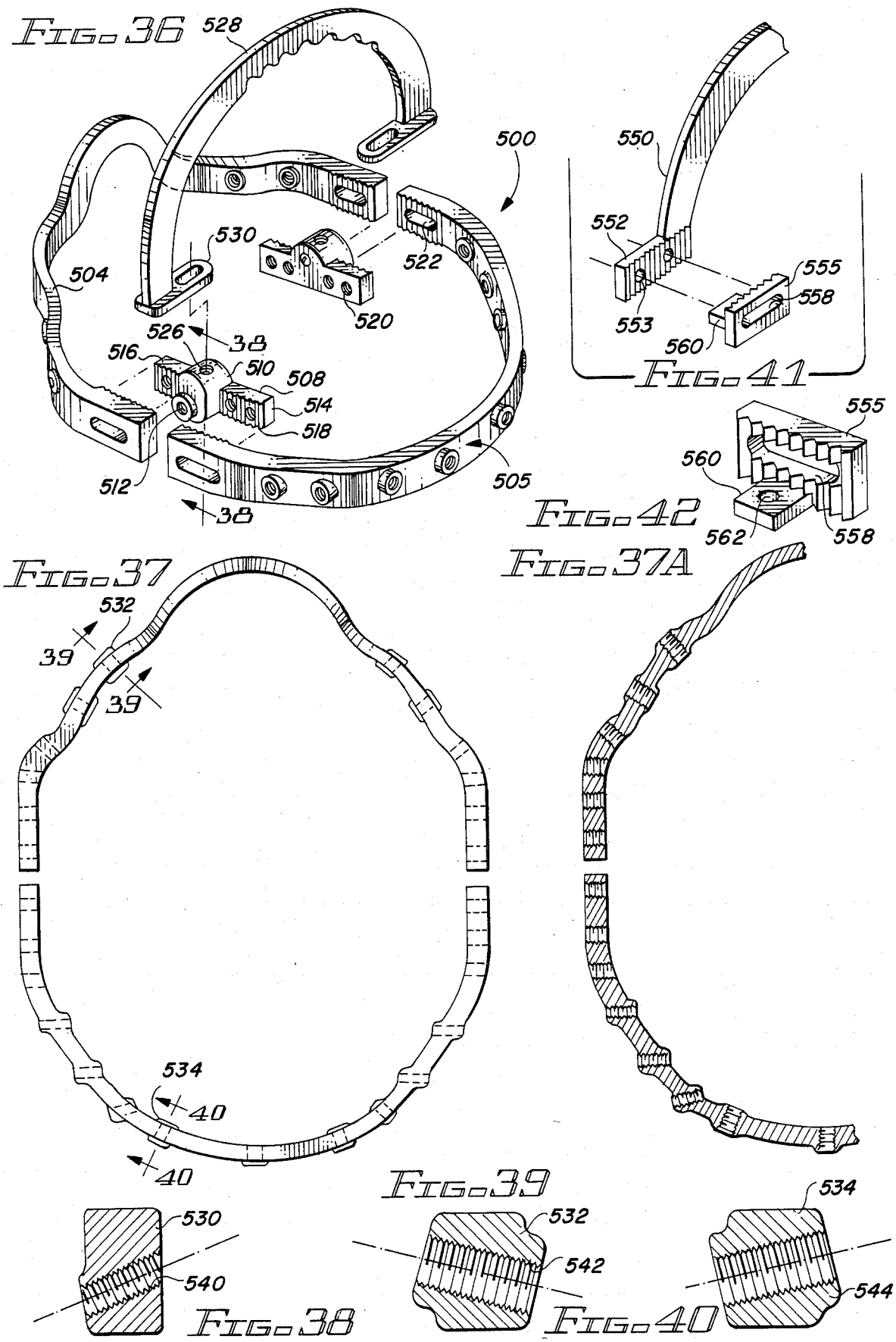

HALO TRACTION BRACE

The present invention relates to a cervical brace for immobilizing the cervical spine. The brace includes a halo for applying traction to the patient's head which halo is supported from a vest worn about the body of the user.

Various devices can be found in the prior art for immobilization of cervical vertebrae in the treatment of traumatic injury to this area. For example, the early patent to Kroetz, U.S. Pat. No. 1,301,276, shows a support for the correction of malposition of the cervical vertebrae having an extensible occipital chin support which operates in conjunction with a support about the body of the user.

Later developed apparatus for the immobilization of cervical spine fractures utilized a plaster jacket unit for supporting a halo. Some apparatus incorporated an overhead framework for suspending a halo or other cervical traction frame as is shown in U.S. Pat. No. 2,649,856 to Schmerl. A somewhat similar overhead suspension apparatus for adjustably immobilizing a patient's head in a predetermined position while treating a fracture or dislocation of the cervical spine is shown in U.S. Pat. No. 3,336,922.

More recent approaches to the problem of treating cervical trauma utilize suspension consisting of a stainless steel halo ring which is positioned around the head of the patient and is attached to the skull by means of skull pins inserted through threaded holes in the halo ring. Axial adjustment of the pins changes the position of the patient's head relative to the spine so that the proper alignment can be achieved. The halo ring is generally supported by a frame arrangement extending from a vest worn about the body of the user. U.S. Pat. No. 3,957,040 shows a cervical brace which includes means for pivotally connecting spaced locations on a shoulder-embracing support to three spaced mating locations on the head-embracing portion of the brace.

U.S. Pat. No. 4,541,421 shows another halo fixation system utilizing an orthopaedic jacket with an attached halo assembly. The halo fixation system includes ball and socket assemblies which support the halo for adjustment. The jacket includes a front and rear portion conforming to the body with straps and locking buckles for adjustably securing the jacket about the patient's waist.

While the foregoing cervical traction apparatus are effective to immobilize and treat cervical spine fractures, certain disadvantages exist with such devices. Many of the devices are not compatible with current X-ray, CAT Scan and NMR medical procedures. Further, the ideal cervical traction of the halo type should be easy to apply and should provide a full range of adjustment. Further, prior art vest configurations for supporting the halo are often uncomfortable for the patient to wear as they apply pressure to the user's body resulting in discomfort which can be corrected only by cutting or re-molding the vest. Prior art halo assemblies utilizing a vest often severly restrict the freedom of movement of the user and require special equipment and special hospital procedures to apply the halo and vest. Further, the design of conventional halo rings often is not compatible with the shape of the user's head and, accordingly, the resulting orientation of the skull pin does not provide optimum securement of the pins to the skull.

Accordingly, there exists a need in the prior art for improved cervical traction device of the type utilizing a skull-encircling halo supported from a torso-encircling vest which device is compatible with medical X-ray, CAT scan and NMR procedures and which is convenient and efficient for application and which provides the wearer freedom of movement and comfort.

Accordingly, it is a primary object of the present invention to provide a halo support vest which is compatible with the anatomy of the wearer and which exerts a securing force toward the sagittal plane of the body.

Another object of the present invention is to provide a halo ring which better conforms to the shape of the skull of the user for better securement of the skull pins.

Still another object of the present invention is to provide a halo fixation system which is modular, lightweight and which utilizes state-of-the-art materials.

A further object of the present invention is to provide a halo fixation system which is easily utilized by medical personnel and which is easily fitted and adjusted to apply traction, angulation, rotation, and translation procedures.

A more complete understanding of the present invention will be had from the following description taken in conjunction with the accompanying drawings in which:

FIG. 2 is a side view showing a patient's head and upper body in dotted lines with the halo and supporting structure in position;

FIG. 3 is a perspective view of a skull pin;

FIG. 4 is a perspective view of the neck support as indicated in FIG. 2;

FIG. 5 is a top view of the neck support shown in FIG. 4;

FIG. 6 is a plan view of the halo ring shown in FIG. 2;

FIG. 7 is a front view of the halo ring shown in FIG. 6;

FIG. 8 is an sectional view of the halo ring taken along lines 8—8 of FIG. 6;

FIG. 9 is a perspective view of the halo ring and attachment assembly;

FIG. 10 is an exploded view of the assembly for securing the halo ring to the attachment rod as seen in FIG. 9;

FIG. 11 is a detail view of the universal connection at the front of the vest as seen in FIG. 1;

FIG. 12 is a sectional view taken along line 12—12 of FIG. 1;

FIG. 13 is a detail view as indicated in FIG. 12;

FIG. 14 is a sectional view taken along line 14—14 of FIG. 1;

FIG. 15 is a sectional view taken along line 15—15 of FIG. 1;

FIGS. 16, 16A are sectional views of the vest buckle assembly as indicated in FIG. 1 with the buckle in a closed position in FIG. 16 and an open position in FIG. 16A;

FIG. 16B is a detail view of the adjustable clasp portion of the buckle assembly shown in FIGS. 16 and 16A;

FIG. 17 is a sectional view taken along line 17—17 of FIG. 1;

FIG. 18 is an exploded perspective view of an end portion of the vest shown in FIG. 17;

FIG. 19 is a sectional view taken along line 19—19 of FIG. 1;

FIG. 20 is a sectional view taken along line 20—20 of FIG. 1;

FIG. 20A is a sectional view of the tongue and buckle shown in FIGS. 19 and 20 in an engaged position;

FIG. 21 is a detail of the support bar shown in FIG. 1;

FIG. 21A is a view of the support bar as shown in FIG. 21 with the locking sleeve in an extended position;

FIG. 22 is a perspective view of an alternate support bar arrangement utilizing non-ferrous materials;

FIG. 23 is an exploded view of the support bar arrangement of FIG. 22;

FIG. 24 is a sectional view taken along line 24—24 of FIG. 22;

FIG. 25 is omitted.

FIG. 26 is a detail view illustrating an alternate arrangement for adjustably securing the skull pin to the halo ring;

FIG. 26A is a sectional view taken along line 26A—26A of FIG. 26;

FIG. 27 is a sectional view taken along line 27—27 of FIG. 26A;

FIG. 28 is a perspective view of the upper anterior portion of the vest in conjunction with an optional chin support;

FIG. 29 is a perspective view of the chin support shown in FIG. 28;

FIG. 30 is a perspective view of an optional halo ring and temporary traction support;

FIG. 31 is an exploded view of the tong attachment assembly shown in FIG. 30;

FIG. 36 is a perspective view of another halo and traction support;

FIG. 37 is a plan view of the halo shown in FIG. 36;

FIG. 37A is a sectional view of the halo shown in FIG. 37;

FIG. 38 is a sectional view taken along line 38—38 of FIG. 36;

FIG. 39 is a sectional view taken along line 39—39 of FIG. 37;

FIG. 40 is a sectional view taken along line 40—40 of FIG. 37; and

FIGS. 41 and 42 show an alternate arrangement for securing the loop to the halo ring.

Figure 1:
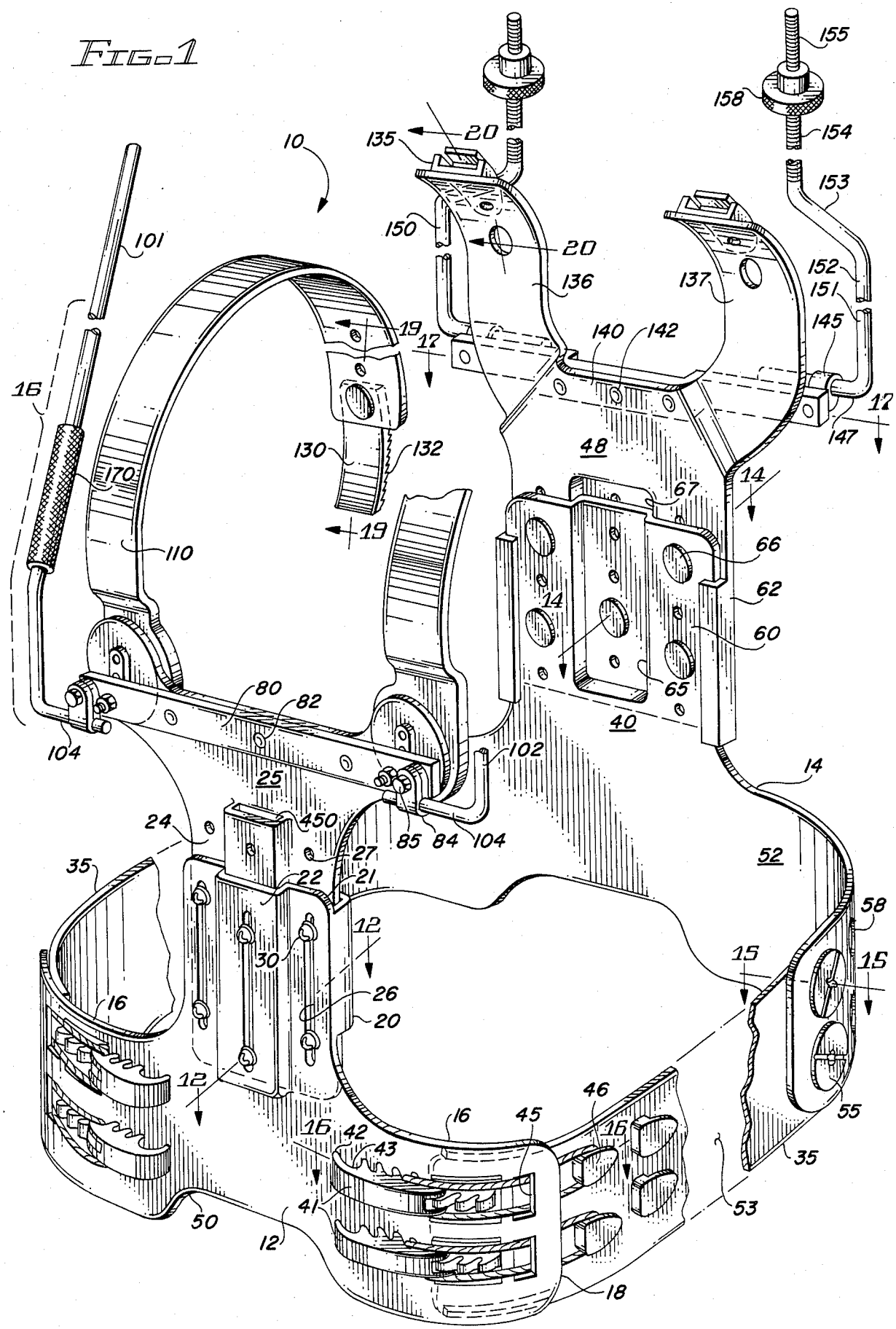
FIG. 1 is a perspective view of the vest portion of the halo fixation system of the present invention.
Figure 32:
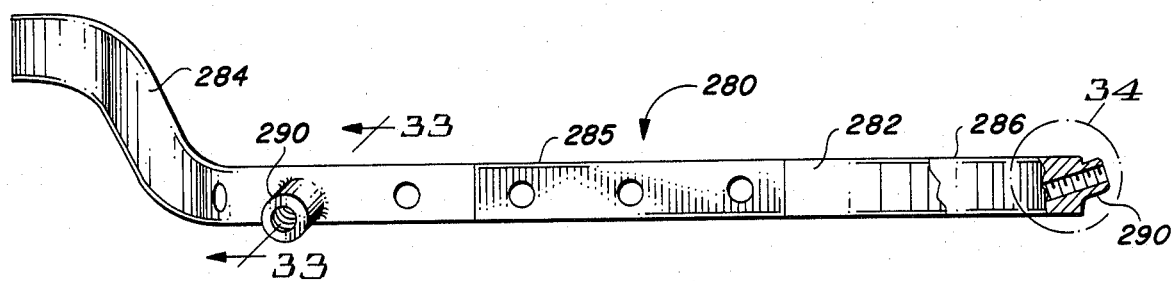
FIG. 32 is a side view of another embodiment of the halo.

Turning now to the drawings, FIG. 1 illustrates the vest portion of the cervical brace and fixation system of the present invention. The vest may be used to support halo rings of various construction and the individual halo ring construction will be more fully described hereafter. The vest is generally designated by the numeral 10 and includes a front or anterior portion 12 and a rear or posterior portion 14. The front vest portion 12 is preferably molded from a synthetic material such as polyethylene or polyurethane and has belt 16 generally extending across the upper abdominal area of the user terminating at opposite ends 18 in the area of the external oblique muscle. Bracket 20 is supported by belt 16 in an area generally corresponding to the upper abdominal area of the user to provide vertical adjustment for the front shoulder yoke as will be more fully explained hereafter. As seen in FIGS. 1 and 12, bracket 20 defines a vertically-extending central channel 22 which is provided with flanges 21 at opposite sides to slidably receive lower tongue end 24 of the yoke assembly 25.

Vertically extending slots 26 are in registry with apertures 27 in the yoke portion 25 to provide vertical adjustment of the yoke assembly relative to the belt 16. A plurality of fastener assemblies each consisting of bolt 30, washer 31 and nut 32 extend through aperture 27 and slots 26 as best seen in FIGS. 1 and 13. Thus, the vertical position of yoke assembly 25 can be adjusted by loosening bolts 30 and adjusting yoke assembly 25 relative to bracket 20 and thereafter tightening bolts 30 to secure the yoke assembly at the desired position Vest 10 also includes a posterior belt portion 35 extending oppositely from posterior portion 40. Posterior belt portion 35 is adjustably securable to belt 16 at buckle members 41 which are hinged or pivotally secured to belt 16. Buckles 41 are shown in detail in FIGS. 16, 16A and 16B, have an over-center lever 42 and are provided with a plurality of notches 43 which engage one end of bail 44 at a selected position. Bail 44 extends through an aperture 45 with the opposite end of bail 44 engageable about a hook 46 on belt portion 35. FIG. 16 shows a buckle 41 in a closed position with the lever in an over-center position. Multiple buckle assemblies may be provided at either side for more precise and better adjustment. By selectively engaging bails 44 at the appropriate post 46 at one end and a selected notch 43 on the lever 42 at the other end, precise circumferential snugness of the vest may be obtained. The buckle is opened as shown in FIG. 16A by pivoting lever 42 to release the bail. The belts 16 and 35 are preferably about four to six inches in width and are suitably flexible to conform to the anatomy of the user. The lower edge of anterior portion 12 is provided with a central cut-out 50 to relieve pressure in the area of the diaphragm of the user.

Posterior vest portion 14 has opposite sections 52 which extend across the back of the user in the lower thoracic area. Side sections 53 are joined to the rear sections 52 by fasteners 55 which extend through holes 58 at opposite edges of rear belt portion 52 as shown in detail in FIG. 15. Additional circumferential or girth adjustment can be obtained by selectively positioning fasteners 55 in the desired openings 58 in the belt. A principal advantage is that the belt arrangement described above allows the vest to be tightened laterally inwardly toward the sagittal plane of the body thus relieving pressure to the abdominal and diaphragm areas occasioned by conventional vest closure arrangements.

As seen in FIGS. 1 and 14, tongue 60 extends vertically from the rear central area of posterior vest section 14 and is received within bracket 62 carried on the lower end of the rear shoulder harness 48. Tongue 60 has a central vertical projection 65 received within a recess 67 in harness 48 to guide the relative vertical adjustment between these two components. The components can be secured within the range of adjustments by fasteners 66. The overall construction of the adjustable bracket 62 generally corresponds to that of bracket 20 described above and further detailed discussion is not believed necessary.

Front transverse reinforcing bar 80 is attached by appropriate rivets or other fasteners 82 to anterior yoke assembly 25. The opposite ends of bar 80 each carry a U-shaped bracket 84 which is secured to the bar by bolt 85. The lower end of frontal support bar assemblies 101, 102 each are provided with inwardly turned leg 104 which is received within bracket 84 and which may be laterally adjusted with respect to bracket 84 and secured in the desired position. A pair of anterior shoulder harness members 110 and 112 are secured to yoke 25 and joined thereto above transverse support bar 80. Referring to FIG. 11, it will be seen that the lower ends of each of the anterior shoulder harness members 110, 112 terminate at a socket 114 which receives the curved surface of semi-spherical ball 116. L-shaped bolt 118 is secured to the outer planar surface of balls 116 having threaded end 120 which is received within bore 121 at the terminal end of the bracket 80 A collar 122 is provided on the shank of the bolt so that the bracket and bolt may be secured by nut 125. Ball 116 can be moved horizontally, vertically or rotated within the socket 114. Accordingly, each of the harness members 110, 112 which extend over the shoulder area and down the trapezius muscle of the wearer may be adjusted to fit the anatomy of the user, particularly providing adjustment in the deltoid pectoralis major muscle area.

The distal or outer ends of the harness members 110 are each provided with a tongue 130 having a plurality of transversely extending grooves 132 on one surface of the tongue. The tongues are adjustably receivable within buckles 135 secured to the upper end of strap portions 136 and 137 at opposite sides of the posterior portion 40. It will be seen that harness members 110 and 112 are securable to the 7 corresponding rear strap 136 and 137 at buckle and tongue 130 and 135, respectively. The grooves 132 are selectively engageable with the buckle to provide length adjustment as is shown in detail in FIGS. 19, 20 and 20A.

A support bar 140 extends transversely across the rear vest section 48 at a location above the projection of the scapula. For comfort, the opposite ends of the bar may be rearwardly recessed away from the body of the user. Bar 140 is secured to the yoke 48 by appropriate rivets or other fasteners 142. Each end of the bar 140 carries a clamp 145 which is secured to the bar by a fastener 146 as best shown in FIGS. 1, 17 and 18. The clamps 145 accomodate the lower horizontal ends 147 of rear support rods 150 and 152. The rear support rods each are constructed having a horizontal lower end 147, a vertical section 151, inwardly converging section 153 and a upper distal end 154 which is provided with threads 155 which carry lock nuts 158. It will be seen that the spacing and relative lateral position of the rear support rods 150 and 152 may be selectively adjusted at clamp members 145 by moving rod sections 147 relative to clamps 145.

The front support rods 101 and 102 are best seen in FIGS. 1, 2, 21 and 21A and each have horizontally, inwardly turned lower leg 104, vertically extending section 160 and an intermediate angular section 162 which extends inwardly toward the wearer forming an acute angle with respect to section 160. A second section 164 is axially aligned with section 162 and is pivotally connected thereto at pivot connection 165. A cylindrical sleeve 170 is slidable along sections 162 and 164 when they are axially aligned. With sleeve 170 in the position shown in FIG. 21A, pivot connection 165 allows rod section 164 to rotate as indicated by the arrows for release from the bracket 174 secured at section 154 on the corresponding rear rod as seen in FIG. 2. When the sleeve 170 is moved downwardly as shown in FIG. 21, sleeve 170 serves to lock support sections 162 and 164 in axial alignment.

The foregoing description relates to the vest and rod support portions of the halo fixation system. A preferred embodiment of the halo is illustraated in FIGS. 6 through 10. The halo assembly consists of a halo ring 175 and bracket assembly 181 secured at opposite lateral sides of the halo and attachable to the upper vertical ends 154 of support rods 150 and 152. Halo 175 consists of opposed pair of lateral or temporal sections 176 and 177, a posterior superior loop 180 and anterior segment 182 all integrally joined to form the halo. The posterior loop 180 extends to the area of the parietal bone to provide medical personnel access to the rear of the skull for medical treatment. The opposite temporal sections are generally horizontally disposed when in position. The anterior segment 182 is disposed at an angle of approxiamte 12° with respect to the lateral segments 176 and 177 as best illustrated in FIG. 8. A plurality of threaded bores 183 are provided at spaced locations in the halo, generally perpendicular to the outer surface of the halo ring. Thus, when skull pins 185 as shown in FIG. 3 are placed in the bores 183, particularly in the frontal segment 182, the pins will assume a position generally perpendicular to the area of the skull immediately adjacent the ring with the threaded body portion 186 of the pin engaging threaded bores 183 in the halo. The point 188 of the pin is brought into contact with the patient's skull and is generally perpendicular thereto. Since the frontal bone curves inwardly and rearwardly in the area generally encompassed by halo anterior segment 182, the point 188 of the pins in the frontal area will engage the halo skull to better secure the ring without slipping or damage to the skin of the patient. Similarly, the pins located in the lateral and posterior halo section will also engage the skull for better securement reducing the possibility of slippage.

The halo 175 is secured at opposite temporal sections 176 and 177 by a pair of bracket assemblies 181 disposed at the upper end of each of the rear support rods 150. The bracket assembly 181 is best seen in FIG. 10. The rear support rods 150, 152 are threaded at their upper ends and adjusting nut 158 is in threaded engagement with the rod. Clamp 192 defines a vertical bore 194 which receives the upper end of rods 150, 152. Threaded bore 196 extends transversely with respect to vertical bore 194. Radial star teeth 195 are provided about the bore 196 to permit angular adjustment of angle bracket 200. Angle bracket 200 has perpendicular legs 202 and 204 provided with bores 206 and 208, respectively. Leg 202 is provided with radial star teeth 210 which are engageable with teeth 195 on bracket 192 to provide angular adjustment between the two elements. Bolt 212 extends through leg 202 engaging threaded bore 196 of bracket 192 to secure the angle bracket and clamp 192 together and further to secure the clamp at the proper height about the upper end 155 of the rear rods. The opposite leg 204 of the angle bracket is provided with radial star teeth 226 which are engageable with teeth 230 on adapter 232. Adapter 232 is provided with a bore 234 through which bolt 215 passes to engage a selected threaded bore 183 in the halo 175 as best seen in FIG. 2. The inner surface of adapter 232 defines a slot 236 so that the adapter will engage the opposite edges of the halo member and not rotate relative to the halo ring. The front support rods 101 and 102 are attached to the rear rods at bracket 174 as seen in FIG. 2.

Thus, it will be seen that with the adjustments provided at the halo vest, the vest can be efficiently and comfortably fitted to patients of varying anatomical sizes and shapes. The vest being of a soft synthetic material is flexible but yet provides stability for the superjacent halo. The belt portion of the vest which extends around the torso of the user may be selectively tightened so that the belt tightens laterally inwardly toward the saggiatal plane relieving pressure in the area of diaphragm.

FIGS. 26, 26A and 27 show an alternate arrangement for attaching the skull pins to the halo ring 262 so that they may be properly positioned relative to the skull. In this embodiment vertically elongated slots 240 are provided at spaced apart peripheral locations in the halo ring 262. Adjacent the opposite edges of slots 240, trunions 242 and 244 are integrally formed with the halo ring. Each trunion 240, 242 defines a threaded bore which receives studs 246 and 248 which oppositely extend from cylindrical body member 250 positioned between the trunions. The ends of the studs 246, 248 each are in threaded engagement with nuts 251. The outer ends of each of the studs are provided with a recess 252 for receipt of an Allen wrench or similar tool.

A transverse threaded bore 255 extends through body member 250 in alignment with slot 240 in the halo. Skull pin 260 is in threaded engagement in threaded bore 255 as best seen in FIG. 26. The inner end of the skull pin is provided with a pointed end 261 for engagement with the patient's skull as is conventional.

It will be apparent that the angular position of the skull pin relative to the skull can be adjusted by rotating the body member 250 on studs 246, 248. When the desired angular position is obtained, the body member 250 can be locked in place by tightening nuts 251 securing the studs from rotation by insertion of an Allen wrench or similar tool in recess 252. Skull pin 260 can then be advanced or retracted in bore 255 until the point is in proper engagement with the patient's skull preferably generally perpendicular to a tangent to the skull at that location.

Figure 33:
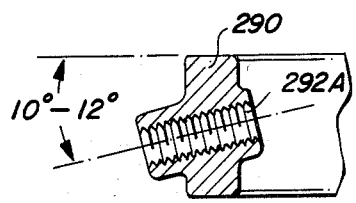
FIG. 33 is a sectional view taken along line 33—33 of FIG. 32.
Figure 34:
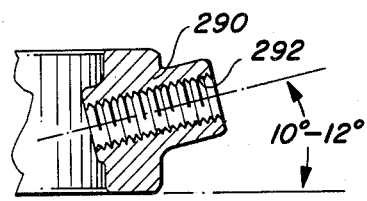
FIG. 34 is enlarged view as indicated in FIG. 32 34—34 of FIG. 32.
Figure 35:
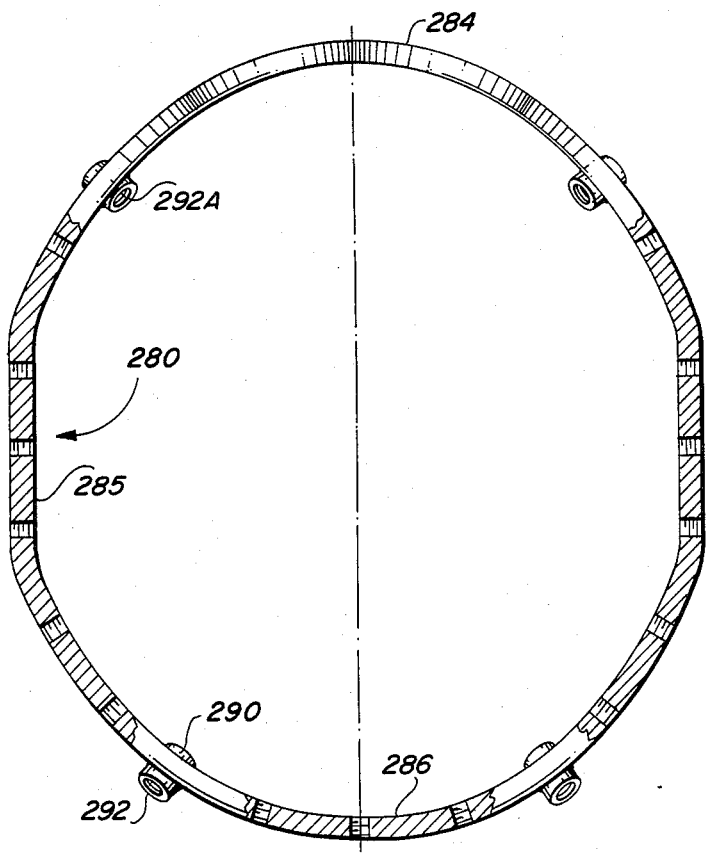
FIG. 35 is a plan view of the halo shown in FIG. 32.

Another embodiment of the halo ring is illustrated in FIGS. 32 to 35. This embodiment is generally designated by the numeral 280 and the halo ring 282 is generally configured as has been described with reference to the previous figure having an elevated posterior section 284, opposite lateral or temporal sections 285 and a frontal segment 286 to generally conform to the shape of the human skull. Bosses 290 are integrally formed at spaced apart locations on the frontal and posterior halo section. Bosses 290 are provided with threaded bores 292 as best seen in FIG. 34. The bores 292 in the frontal area are angularly disposed with respect to the lower edge surface of halo segment 282 so that the skull pins when inserted will engage the adjacent portion of the skull in a generally normal position. The angular disposition of the bores 292 will vary with the position of the bore on the halo ring. For example, in the normal skull configuration, bores 292 at the frontal section will generally be angled upwardly between 0° and 12° as seen in FIG. 34. The threaded bores 292A in the posterior segment of the halo ring as indicated in FIG. 33 are preferably downwardly angled 10° to 12° for best pin engagement with the skull. The bosses and bores in the opposite temporal sections 285 will be generally perpendicular to the inner side of the halo. The angularity of the bores is selected so that the pins engage the skull in a generally perpendicular orientation.

Another significant advantage of the present invention provides for a halo support system which is compatible with computer tomography (CT), nuclear magnetics resistance (NMR), and X-ray techniques. In many cases, the use of stainless steel or other ferrous material interferes with these medical procedures and use of alternate materials such as nylon, plastics, hardcase aluminum and titanium is preferable. Accordingly, FIGS. 22 to 25 illustrate an alternate construction for the rear support rods which utilize primarily non-ferrous materials. In this case, the associated halo is preferably constructed from non-ferrous material such as hardcase aluminum or a carbon graphite material. The problem with many non-ferrous materials, particularly nonmetallic materials such as carbon graphite, is the difficulty of attaching brackets and other mounting hardware to the rods as these materials are not suitable for placement of threads. Accordingly, as shown in FIGS. 22 to 24, the halo support rods are formed of a suitable nonferrous material such as nylon, fiberglass or carbon graphite and are designated by the numeral 300. A threaded non-ferrous tube 302 is engageable over rod 300. The lower end of tube 302 is provided with a longitudinally extending slot 304. A lock nut 305 is engageable about the threaded tube 302. The threaded tube 302 may be positioned at any suitable axial position along rod 300 and nut 305 tightened causing the rod in the area of the slot 304 to tightly engage rod 300. Adjustable sleeve 310 has an integrally formed lock nut 312 at its lower end in threaded engagement with tube 302. Preferably sleeve 310 and lock nut 312 are of a suitable nonmetallic material such as plastic or nylon. The upper end of sleeve 310 supports clamp 330 which has a threaded member 322 with longitudinal slots 230 which defines an axially extending bore 325 which is slidable over the upper end of rod 300. Clamp 330 includes a pair of opposed faces 326, 327 having radially extending star grooves or teeth therein which are engageable either with an adapter 331 having a recess 332 engageable with the halo 175. In the alternative, the grooved star surfaces 326 and 327 may be engageable with a corresponding surface 335 directly formed or molded in the surface of halo 175A. A bolt or other appropriate fastener, not shown, may be extended through bore 342 in clamp 330 to secure the bracket to the halo at threaded bore 183 or 183A. Lock nut 350 is in threaded engagement with threaded section 322 of the clamp 330 to compress section 322 about rod 300 and secure the clamp in the desired position. With the construction described above, the use of ferrous materials which would interfere with certain medical procedures described above is minimized. Further, the construction allows full vertical adjustability of the halo through adjustment at tube 302 and sleeve 310. Angular adjustment is obtained at clamp 330 which may be rotated about threaded section 322 and locked in position by nut 350.

As seen in FIG. 2, the front support bars are connected to the rear support bars at bracket 174. As has been described above, the front support bars are provided with a locking sleeve 170 which, when moved upwardly, allows the front support bars 101 and 102 to be quickly disengaged from the associated rear bar. The front support bars connect to the rear support bars in an area generally corresponding to the steronciedomastoid muscle. As best seen in FIGS. 2, 4 and 5, a rearwardly extending bracket 375 is in threaded engagement with the upper section of rear support rods 150 and 152. The brackets 375 define a horizontal bore 376 for receipt of support rod 378 having an off-set central section 380. A neck brace or pad 382 is secured to the off-set rod section by a clamp 384. The brace is preferably padded and transversely curved to conform to the anatomy of the user in this area. As best seen in FIG. 4, it will be seen that the relative forward and rearward position of the pad 382 is adjustable by rotation of the rod 378. In addition, pad 382 is also rotatable about the axis of recessed central portion 380 of support rod 378 to provide additional adjustability in accordance with the physical requirements of the patient and the requirements of the treatment.

In some medical situations, a patient recovering from a cervical injury can, after sufficient time in the halo, have the halo removed with sufficient cervical stability provided by non-invasive mandible and occipital supports. The present invention is modular in that various components may be removed and replaced by other components as dicated by the medical treatment. As shown in FIGS. 28 and 29, modular mandible and occipital supports can be utilized with the vest portion of the present invention. The upper front portion of the vest is a yoke assembly indicated by the numeral 5 and is as has been more fully described in FIG. 1. The bracket 20 defines a vertically extending channel 22 which has a slot 400 which removably receives tongue 402. The upper end of tongue 402 defines a clevis 406 having a threaded rod 408 in engagement with internally threaded sleeve 410. The upper end of sleeve 410 is in threaded engagement with member 412 which is pivotally secured to the underside of support 420. Support 420 is generally curved to conform to the configuration of the mandible portion of the anatomy. Suitable padding 425 may be provided on the interior surface and straps 426 may be secured to the support for attachment about the head of the user to further restrain the cervical area from undesirable movement. The vertical position of the support is adjusted by rotating sleeve 410 to extend or shorten the effective overall length of the support. Similarly, the clevis arrangements at either end of sleeve 410 allow for forward and rearward adjustment of the support.

In FIG. 29 a support for the occipital area is provided which is similar in construction to the mandibular support having a head-engaging shell 440 generally conforming to the shape of the posterior portion of the cranium. The shell 440 is secured to a tongue 445 through a clevis arrangement 446 on the support which, in turn, is engageable within an elongated threaded nut 449. Clevis 446 on the tongue 445 also pivotally supports a threaded rod 448 which is in threaded engagement with the lower end of the threaded nut 449. Tongue 445 is supported at slot formed as a part of recess 67. A full range of adjustments can be obtained in accordance with the requirements of the user and the medical treatment to support and restrain the user's head.

In some medical situations, tongs will be used initially because of their ease of application in emergency treatment procedures. It is often necessary to initially use a bail or temporary loop for traction. The halo ring of the present invention is useable with tongs and a temporary bail or loop for traction. The tongs and bail can be removed when desired leaving the halo in position which halo can then be secured to the head of the user by skull pins. Thus, the medical attendant does not have to decide whether he or she initially wishes to use traction as traction can be accomplished through a temporary loop attachable to the halo ring. Similarly, Crutchfield tongs or other tongs can be initially used with the halo ring and removed from the halo ring leaving the ring in place ready for securement to the patient making the transition much more efficient and less traumatic to the patient.

FIGS. 30 and 31 show a modified halo ring generally designated by the numeral 500 and which includes a continuous halo ring 502 having opposite temporal sections 504, frontal loop 506 and posterior loop 508. Tapped bores 510 are provided at spaced-apart locations in the halo. As has been described with reference to the preceding embodiments, the bores 510 are oriented so that skull pins placed in the holes will be generally normal to the user's skull for better engagement. Temporary tongs 520 may be used with the halo ring and removed after initial emergency procedures have been completed. The tongs 520 are of conventional design such as Crutchfield tongs or other tongs well known in the medical field. The tongs are secured to the halo by a bracket 525 which is securable to the halo at threaded holes 528 which can be positioned to align with selected tapped holes 510 in the temporal sections of the halo ring. Appropriate fastener 530 secures the brackets 525 to opposite sides of the halo ring. Bracket 525 defines a circular opening having teeth 534 about its interior. Teeth 534 engage external teeth 536 on bushing 540. A flange 542 on bushing 540 engages the inner surface of the bracket. The tong assembly 520 includes a skull pin 545 having a threaded body which engages cooperating internal threads in adjusting members 550, 552 and bushing 540. Thus, pins 520 can be advanced or retracted by rotation in the appropriate direction once the desired position is achieved, may be locked in place by tightening adjusting nut 552. As is conventional, one of the opposed tongs may be spring loaded in order to achieve proper application of force.

Temporary bail or loop 560 may be supported from ring 565 having a toothed circular opening 568 engageable on the exterior 536 of bushing 540. Ring 565 includes an upwardly extending bracket 570 having a bore 572 therein. The inner face of bracket 570 is provided with star teeth 575 which cooperates with similar star teeth 580 on the lower end of bail or loop 560. Thus, the relative angular position of the temporary loop 560 relative to the halo 502 can be adjusted and when the desired position obtained, the loop 560 secured in place by fastener 586 extending through bore 572 into threaded bore 588 at the end of the loop. The loop 560 may further be provided with an eye bolt 590 at the apex of the loop for attachment to an external traction system.

FIGS. 36 to 40 illustrate another embodiment of a halo adapted for use with tongs and a temporary support loop. The halo is generally designated by the numeral 500 and has a separate anterior segment 505 and posterior segment 504 which are joined at opposite temporal sections by bracket 508. Bracket 508 has a body 510 with a bore 512 adapted to receive conventional tongs, not shown. Arms 514 and 516 extend oppositely from body 510 and define bores 520 which align with elongated slots 522 in the ends of the halo segments. Fasteners, not shown, are used to secure the halo segments to bracket 508 in the desired position.

Temporary loop 528 is semi-circular and extends between brackets 510 and is securable thereto at feet 530 by a bolt or other fastener engageable in bores 526.

FIGS. 37, 37A and 38 to 40 illustrate the segmented halo with integrally formed bosses 530, 532, 534 having angularly disposed bores 540, 542 and 544, respectively, to accomodate skull pins as has been described above.

FIGS. 41 and 42 illustrate another construction for attachment of a temporary loop 550 which terminates at feet 552 having holes 553 therein. Feet 552 are adjustably securable to base 555 which defines a slot 558 alignable with bores 553. A fastener, not shown, is utilized to secure the components. Base 555 includes a flange 560 defining a bore 562 which is securable at bore 526 in member 510.

With the embodiment of FIGS. 37 to 42, the patient may first be placed in traction and critical cervical treatments initiated such as reduction. After initial treatments, the ring is added for additional treatments and may be removed leaving the halo in position.

It will be obvious to those skilled in the art to make various changes, alterations and modifications to the system described herein. To the extent these various alterations, modifications and changes do not depart from the spirit and scope of the appended claims, they are intended to be encompassed therein.

I claim:

1. A cervical brace to be worn on the upper body for stabilizing and immobilizing the head and cervical spine of a wearer comprising:
    (a) a flexible anterior belt portion adapted to extend around the lower costal area of the ribs and terminating at either side of the wearer;
    (b) a flexible posterior belt portion adapted to extend around the lower thoracic lumbar are a of the user and terminating at either side of the user;
    (c) fastener means adjustably connecting said anterior belt portion and said posterior belt portion of the sides of the wearer and adapted to apply a closing force generally perpendicular with respect to the sagittal plane of the body of the wearer;
    (d) front bracket means on said anterior belt portion in the region of the sternum
    (e) rear bracket means on said posterior belt portion in the lumbar spinal area;
    (f) front yoke means carried on said front bracket means and being vertically adjustable relative to said front bracket means;
    (g) rear yoke means carried on said rear bracket means and being vertically adjustable relative to said rear bracket means;
    (h) adjustable strap means extending between said front and rear yoke means adapted to extend over the shoulder of the wearer; and
    (i) a pair of front support rods having upper and lower ends and attached at their lower ends of opposite sides of said front yoke means and a pair of rear support rods having upper and lower ends and attached at their lower ends at opposite sides of said rear yoke means, said front and rear support rods adapted to support a halo at their upper ends.

2. The cervical brace of claim 1 wherein said strap means are joined to said front yoke means at a pivotal connection on said front yoke means, said pivotal connection being located in an area substantially conforming to the deltoid pectoral groove of the wearer.

3. The cervical brace of claim 1 wherein said front yoke has mounting means associated therewith and further including mandibular support means adjustably received in said mounting means.

4. The cervical brace of claim 1 wherein said front support rods include a pivotal joint and locking means for securing said rods in a locked position wherein said rods may be unlocked and pivoted to an unlocked position.

5. The cervical brace of claim 1 further including removable occipital support means adjustably securable at said rear yoke means and adapted to supportingly engage the head of the user.

6. The cervical brace of claim 1 wherein said support rods are non-ferrous and wherein said front support rods are secured to said rear rods at an intermediate position on said rear rods and wherein said rear rods support an axially extending nonferrous sleeve selectively engageable on said rear rods and further including halo bracket means adjustably carried on said sleeve.

7. The cervical brace of claim 1 wherein said flexible anterior belt portion defines a relieved area generally conforming to the diaphragm of the wearer and wherein said flexible belt anterior and posterior portions are fabricated from a pliable material.

8. The cervical brace of claim 1 further including a halo ring adapted to fit around the head of the wearer and attachable to the skull by means of adjustable skull pins and supported on said front and rear support rods.

9. The cervical brace of claim 1 wherein said front and rear support rods are transversely adjustable relative to their said respective yoke means.

10. A halo traction device for mounting skull pins useable with tongs and supportable on support rods attached to an orthopaedic vest worn by the user comprising:
    (a) a halo ring adapted to fit around the skull of the wearer and supportable by rods extending from an orthopaedic vest worn about the body of the user; and
    (b) said halo ring having opposite temporal sections, an anterior loop, and a posterior loop, said halo ring including threaded bores at spaced-apart predetermined locations around said halo ring, said bores having an axis selected to orient the skull pins therein a predetermined locations generally normal to the point of contact with the adjacent skull portion with respect to the circumferential and upward curvature of the cranium.

11. The halo traction device of claim 10 wherein said anterior loop is elevated relative to the temporal sections to provide access to cranium area of the user.

12. A cervical brace to be worn about the upper body of a user for supporting a head-engaging halo at support rods for stabilizing and immobilizing the head and cervical spine of the wearer, said brace comprising:
    (a) an anterior belt portion adapted to extend around the front of the user in the lower costal area of the ribs and terminating at either side of the werer and having a front portion extending upwardly in the region of the sternum;
    (b) a posterior belt portion adapted to extend around the back of the user in the lower thoracic lumbar area and terminating at either side of the user at a location spaced-apart from said anterior belt, said posterior belt having a rear portion extending upwardly in the thoracic region;
    (c) fastener means interconnecting said anterior belt portion and said posterior belt portion at either side of the wearer and adjustable to apply a closing force having a component generally perpendicular with respect to the sagittal plane of the body of the wearer;

(d) front support means on said front portion of said anterior belt and being vertically adjustable relative thereto and having first bracket means therein for attachment of front halo support rods;

(e) rear support means on said rear portion of said posterior belt and being vertically adjustable relative thereto and having second bracket means thereon for attachment of rear support rods; and (f) adjustable strap means extending between said front and rear belt portions over the shoulders of the wearer.

13. A halo traction device for mounting skull pins useable with tongs and supportable on support rods attached to an orthopaedic vest worn by the user comprising:

(a) a traction ring adapted to fit around the skull of the wearer and supportable by rods extending from a vest about the body of the user; and (b) said halo ring having opposite temporal sections, an anterior loop, and a posterior loop, said halo ring including threaded bores at spaced-apart predetermined locations around said halo ring, said bores having an axis selected to orient the skull pins therein at predetermined locations generally normal with respect to adjacent skull portion; and (c) said temporal sections being bifurcated and adapted to be connected by bracket means to receive said tongs therein.

14. The halo traction device of claim 13 further including means associated with said bracket means for detachably securing a transverse loop extending between said opposite temporal sections.

15. A halo for peripheral fixation about the head of a user and supportable upon rods from an orthopaedic jacket, said halo comprising a ring having opposite temporal sections, an anterior section and a posterior loop section, said loop section defining slots therein at spaced-apart peripheral locations, boss means adjacent said slot means and rotatively supporting body means defining a threaded bore therein alignable with said slot means and pin means having a pointed end and in threaded engagement in said bore and axially adjustable with respect to said bore and means for locking said body means in a predetermined angular relationship with respect to said halo to position said pin means relative to the head of the user.

* * * * *